(12) United States Patent
Bornzin et al.

(10) Patent No.: US 9,925,369 B2
(45) Date of Patent: Mar. 27, 2018

(54) RETRIEVABLE INTRAPERICARDIAL ELECTROTHERAPY LEAD

(71) Applicant: PACESETTER, INC., Sylmar, CA (US)

(72) Inventors: Gene A. Bornzin, Simi Valley, CA (US); Didier Theret, Porter Ranch, CA (US); Zoltan Somogyi, Simi Valley, CA (US)

(73) Assignee: PACESETTER, INC., Sylmar, CA (US)

( * ) Notice: Subject to any disclaimer, the term of this patent is extended or adjusted under 35 U.S.C. 154(b) by 0 days.

(21) Appl. No.: 15/143,025

(22) Filed: Apr. 29, 2016

(65) Prior Publication Data

US 2017/0312501 A1    Nov. 2, 2017

(51) Int. Cl.
*A61N 1/05* (2006.01)
(52) U.S. Cl.
CPC .................. *A61N 1/0587* (2013.01)
(58) Field of Classification Search
CPC .................................. A61N 1/0587

USPC .............................. 607/9, 126, 129
See application file for complete search history.

(56) References Cited

U.S. PATENT DOCUMENTS

| | | | | |
|---|---|---|---|---|
| 4,154,247 A | * | 5/1979 | O'Neill | A61N 1/056 607/125 |
| 5,010,894 A | * | 4/1991 | Edhag | A61N 1/3956 607/128 |
| 2013/0116740 A1 | * | 5/2013 | Bornzin | A61N 1/3756 607/9 |

* cited by examiner

*Primary Examiner* — Amanda Patton

(57) ABSTRACT

Disclosed herein is an implantable lead configured to administer electrotherapy to a patient heart from an implantable pulse generator. The lead may include a lead body and an attachment structure. The lead body includes a bifurcated distal region including first and second lead body branches each terminating in a distal end. At least one of the first lead body branch or second lead body branch includes an electrode. The attachment structure couples together the distal ends of the first and second lead body branches. The attachment structure is configured to release such that the distal ends of the first and second lead body branches can decouple from each other.

16 Claims, 11 Drawing Sheets

RETRIEVABLE INTRAPERICARDIAL ELECTROTHERAPY LEAD

TECHNICAL FIELD

Aspects of the present disclosure relate to implantable intrapericardial leads and related methods of explanting such leads.

BACKGROUND

Heart conditions may be treated through the application of electrical stimulation via an implantable pulse generator (IPG) such as, for example, a pacemaker or an implantable cardioverter defibrillator (ICD) that may be used for any type of electrotherapy. The IPG may administer electrical stimulation to the heart tissue via transvenous leads that are located in the vasculature of the patient.

Intrapericardial lead placement offers a number of advantages over transvenous lead placement, including the fact that there is no lead in the vascular system. Unfortunately, intrapericardial leads can be difficult to explant.

There is a need in the art for an intrapericardial electrotherapy lead that is readily explantable. There is also a need in the art for a method of explanting such a lead.

SUMMARY

Disclosed herein is an implantable lead configured to administer electrotherapy to a patient heart from an implantable pulse generator. In one embodiment, the lead includes a lead body and an attachment structure. The lead body includes a bifurcated distal region including first and second lead body branches each terminating in a distal end. At least one of the first lead body branch or second lead body branch includes an electrode. The attachment structure couples together the distal ends of the first and second lead body branches. The attachment structure is configured to release such that the distal ends of the first and second lead body branches can decouple from each other.

In one embodiment, the first and second lead body branches are biased to be spaced apart from each other when the distal ends are coupled together via the attachment structure. The first and second lead body branches may be biased to form a generally oval loop when the distal ends are coupled together via the attachment structure. Each of the first and second lead body branches may be biased to each assume an arcuate shape.

In one embodiment, the lead body includes first and second stylet lumens running parallel to each other. The first stylet lumen extends along the first lead body branch and the second stylet lumen extends along the second lead body branch.

In one embodiment, the lead body includes a single stylet lumen that bifurcates into first and second branch stylet lumens. The first stylet branch lumen extends along the first lead body branch and the second stylet branch lumen extends along the second lead body branch.

In one embodiment, the attachment structure includes a first filament coupling together the first and second lead body branches near the distal ends of the first and second lead body branches. The filament may have a tension strength of approximately 150 grams or 150,000 dynes. The attachment structure may further include a second filament coupling together the first and second lead body branches near the distal ends of the first and second lead body branches. The second filament may have a length that is longer than the first filament.

In one embodiment, the attachment structure includes an interference fit coupling structure. The interference fit coupling structure may include a male member that snap-fits into a female opening. The male member may be part of the first lead body branch near the distal end thereof, and the female opening may be part of the second lead body branch near the distal end thereof In one embodiment, the attachment structure includes a setscrew coupling structure. The setscrew coupling structure may include a setscrew and a male member that is received in a female opening. The setscrew may prevent the male member from withdrawing from the female opening unless the setscrew is unscrewed to release the male member. A head of the setscrew may be accessible via a stylet lumen extending through one of the first or second lead body branches.

In one embodiment, the attachment structure includes a magnetic coupling structure.

In one embodiment, the lengths of the first and second lead body branches are equal. In one embodiment, the lengths of the first and second lead body branches are not equal.

In one embodiment, the electrode includes at least one of a pacing electrode, a sensing electrode or a defibrillation electrode. In one embodiment, both lead body branches include an electrode. In one embodiment, the electrode includes a defibrillation electrode that includes at least one of a metal coil or a smooth, continuous metal surface.

In one embodiment, the lead further includes a lead connector end extending proximally from a proximal end of the lead body. The lead connector end is configured to couple to the implantable pulse generator. The lead connector end may be of an IS-1, DF-1, IS-4 or DF-4 configuration. The lead, or a system employing the lead, may also include the implantable pulse generator.

Also disclosed herein is a method of explanting an implantable electrotherapy lead from an implantation site. In one embodiment, the method includes: decoupling from each other first and second branch distal ends of a bifurcated distal region of a lead body; and withdrawing the lead from the implantation site.

The decoupling may occur a variety of ways. For example, the decoupling may include breaking a filament that extends between the first and second branch distal ends. The decoupling may include causing a snap-fit arrangement between a male member of the first branch distal end and a female opening of the second branch distal end to disengage by the male member leaving the female opening.

The decoupling may include causing a setscrew to release from a male member of the first branch distal end such that the male member can be removed from a female opening of the second branch distal end. A stylet may be extended down a stylet lumen of the lead to cause the setscrew to release the male member.

The decoupling may include overcoming a magnetic bond between the first and second branch distal ends.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

DETAILED DESCRIPTION

Aspects of the present disclosure involve intrapericardial electrotherapy leads that are configured for ease of implantation, stability of the electrode placement once implanted, and to be readily retrievable or explantable. The leads disclosed herein are applicable to a host of electrotherapy applications including, for example and without limitation, CRT, ATP, atrium pacing, etc.

In one embodiment, the leads disclosed herein include an electrode loop at the lead distal end that can be deflected from its biased looped configuration to a narrow elongated arrangement that allows the electrode loop to be readily implantable via implantation methods known in the art, the electrode loop providing a stable arrangement for maintaining the pacing/sensing electrodes and shock electrodes of the electrode loop in constant desirable contact with epicardial tissue of the patient heart when the electrode loop is implanted in the pericardial space. Further, distal ends of the branches of the electrode loop can be selectively decoupled during explant of the lead to allow the electrode loop to open up, thereby allowing the resulting free ends of the branches to slip through tissue without impediment when the lead is pulled proximally by the explanter.

Figure 1:
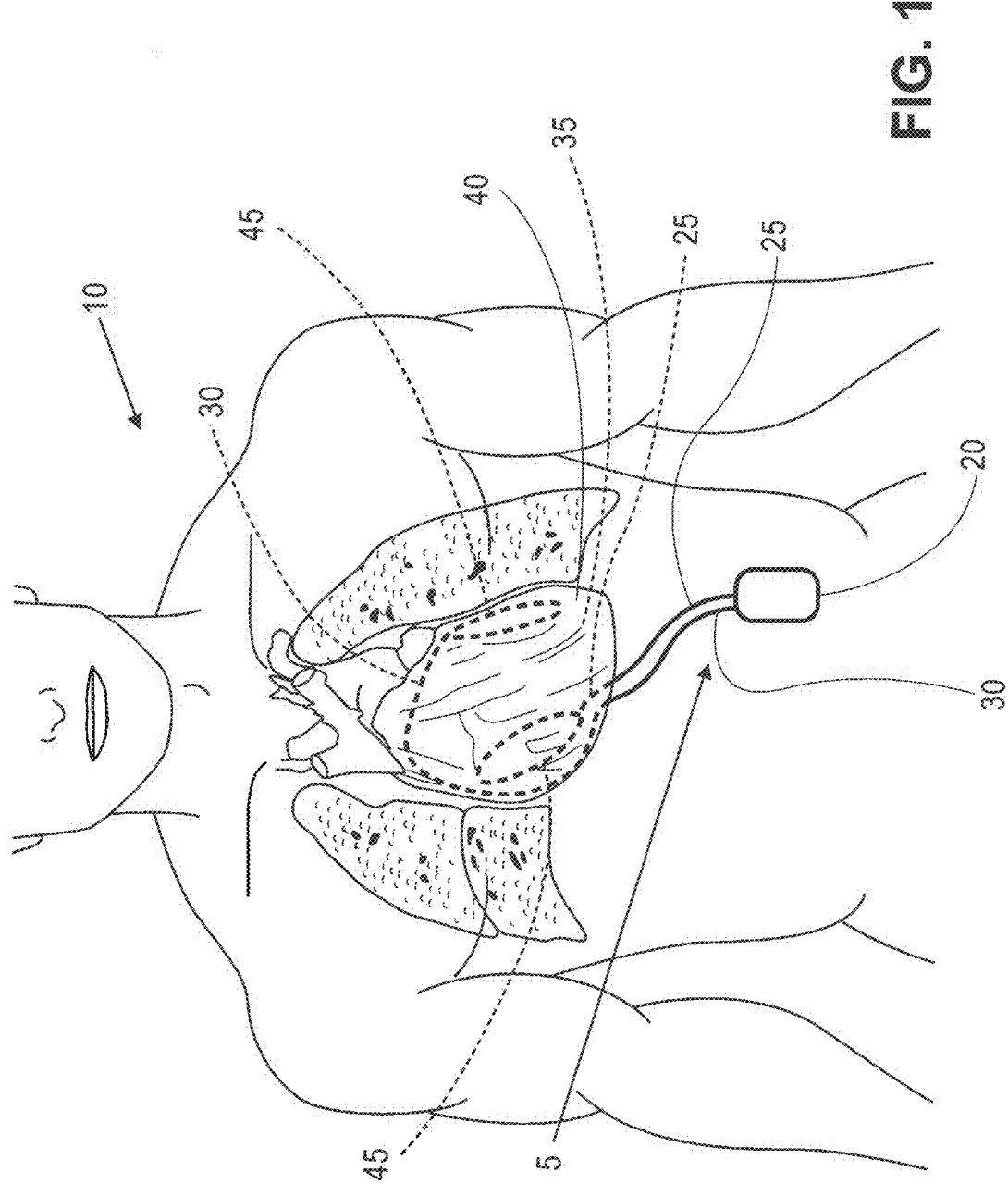
FIG. 1 is a diagrammatic depiction of an implanted electrotherapy system as viewed from an anterior side of a patient.

FIG. 1 is a diagrammatic depiction of an implanted pericardial electrotherapy system 5 as viewed from an anterior side of a patient 10. As shown in FIG. 1, the implanted electrotherapy system 5 includes an IPG 20 and two leads 25, 30 extending from the IPG 20 to implantation locations within the pericardial space and on the patient heart 35. In one embodiment, the IPG 20 is implanted in the patient abdomen, and the leads 25, 30 extend from the IPG 20, through the patient pericardium 40 and into the pericardial space defined between the epicardium of the patient heart 35 and the pericardium 40, the leads resting on the epicardium of the patient heart.

As depicted in FIG. 1, each lead 25, 30, which may be considered an intrapericardial lead, includes a distal electrode loop 45. In one embodiment, the electrode loop 45 of the first lead 25 is located directly on the epicardium at an anterior-lateral region of the right ventricle ("RV"), and the electrode loop 45 of the second lead 30 is located directly on the epicardium at a lateral wall region of the left ventricle ("LV").

As discussed in detail below, a combination of shock electrodes and pacing/sensing electrodes supported on the electrode loop 45 of the RV lead 25 can provide RV anterior-lateral defibrillation and pacing. Similarly, a combination of shock electrodes and pacing/sensing electrodes supported on the electrode loop 45 of the LV lead 30 can provide LV lateral defibrillation and pacing. The pacing/sensing electrodes supported on the electrode loop 45 can even be configured and positioned to act as atrial electrodes to provide VDD or DDD pacing capability. The implant locations illustrated in FIG. 1 have been shown to provide low defibrillation thresholds on the order of 450 volts in pigs, which equates to around 10 Joules.

The leads 25, 30 may be implanted as indicated in FIG. 1 using subxiphoid pericardial access tools and methods as known in the art. For example, in one embodiment, the implanter may access the pericardial space with one of the implant tools and methods disclosed in the following two U.S. Patents, which are both incorporated by reference in their entireties herein: U.S. Pat. No. 8,628,552 to Toy et al., which issued Jan. 14, 2014; and U.S. Pat. No. 9,107,693 to Morgan, which issued Aug. 18, 2015.

In another embodiment, the subxiphoid pericardial access tool is a Touhy needle, and the implanter employs a well-known Touhy needle methodology as follows. First, the implanter inserts the Touhy needle into the patient 10 to the left of the xiphoid process pointed at the left shoulder, and then advances the Touhy needle through the pericardium 35 under fluoroscopic guidance. The pericardium 35 is tented by the needle while contrast injection helps the implanter to determine if the needle is the pericardial space. If the Touhy needle penetrates too deep, it will penetrate into the wall of the RV. When the Touhy needle is properly within the pericardial space, there is contrast staining in between the epicardium and the pericardium that is visible via fluoroscopy. Once the needle is fully and properly advanced into the pericardial space, a guidewire is extended into the pericardial space via the Touhy needle, which is then removed upon proper positioning of the guidewire. An introducer with a dilator is then extended over the guidewire into the pericardial space. The dilator is removed and the leads 25, 30 are advanced one at a time using a retained guidewire technique. The LV lead 30 may be implanted first.

Once the leads 25, 30 are properly implanted within the pericardial space and within the epicardium, the leads are then tunneled to the IPG 20, which is implanted in the patient abdomen, as can be understood from FIG. 1.

Figure 2:
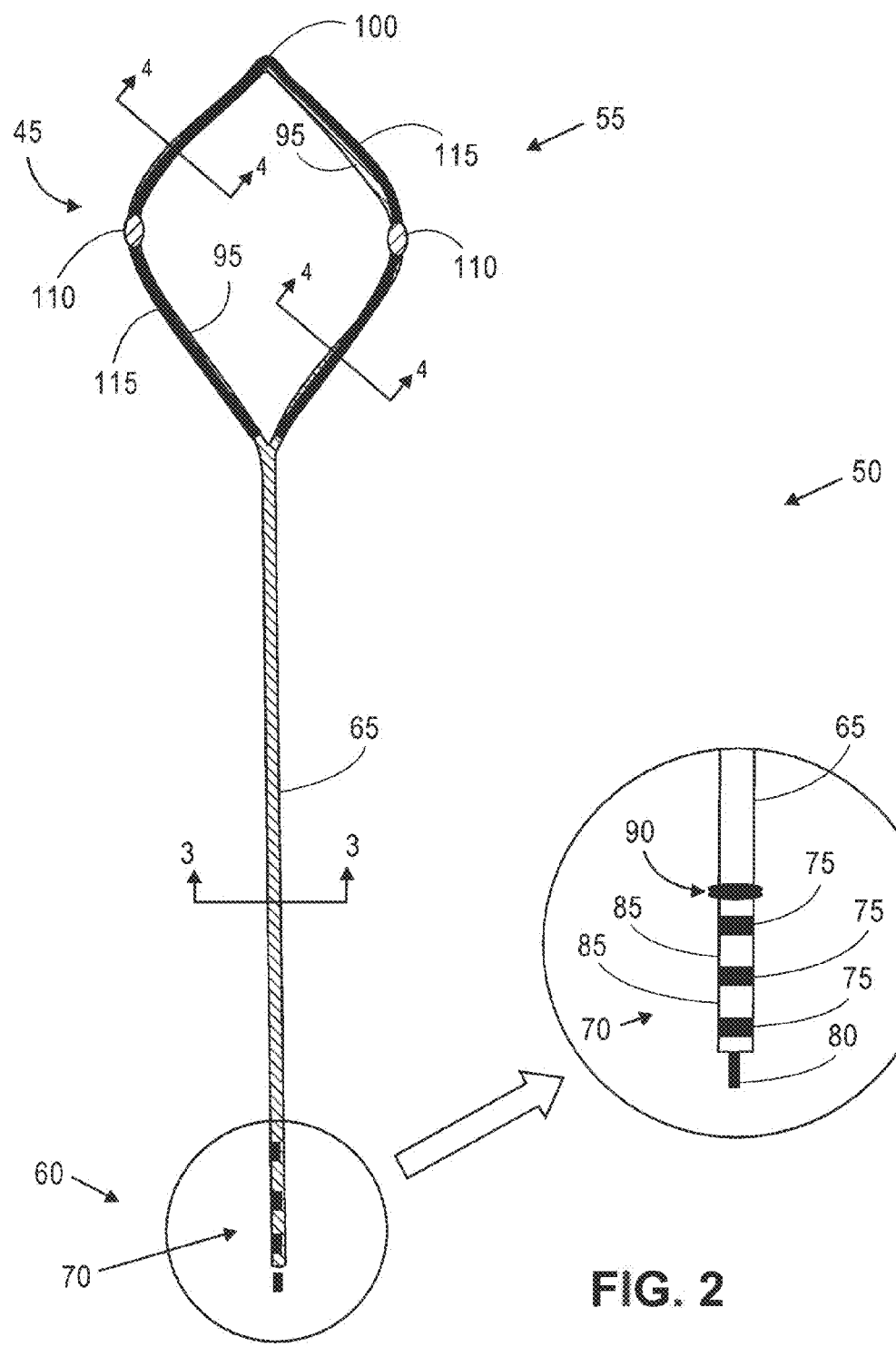
FIG. 2 is a longitudinal side view of an intrapericardial lead that is exemplary of each of the two leads discussed with respect to FIG. 1.

As shown in FIG. 2, which is a longitudinal side view of an intrapericardial lead 50 that is exemplary of each of the two leads 25, 30 discussed above with respect to FIG. 1, the lead 50 includes a distal region 55, a proximal region 60, and a longitudinally extending body 65 extending between the distal and proximal regions. The proximal region 60 includes a lead connector end 70 that defines the proximal terminus of the body 65 and includes a plurality of electrical contacts, which may take the form of ring contacts 75 and a pin contact 80, all of which are separated by electrically insulating regions 85. The lead connector end 70 may take the form of any one of the standard configuration known and used in the industry, including IS-1, IS-4, DF-1, DF-4, etc. In one embodiment, the lead connector end 70 may be bifurcated to provide both a DF-4 lead connector end for defibrillation and an IS-4 lead connector end for pacing.

One or more liquid seals 90 isolate the electrical contacts of the lead connector end 70 from body fluids when the lead connector end is plugged into a receptacle of the IPG 20. The electrical contacts 75, 80 of the lead connector end 70 establishes electrical communication between the electrical conductors extending through the lead body 65 and the electronics contained in the IPG 20, thereby allowing the IPG 20 administer electrotherapy via the pacing electrodes and/or shock electrodes of the lead and sense electrical signals via the sensing electrodes of the lead.

As illustrated in FIG. 2, the distal region 55 of the lead body 65 is bifurcated such that it splits into two legs or branches 95. The branches 95 are joined together proximally where they begin to split the body 65 and also distally at a distal end 100 of the lead 50. The branches 95 are biased to be spaced apart from each other, each branch 95 assuming an arcuate or semi-circular configuration in its relaxed state when not acted upon by an outside force. Since the branches 95 are joined to each other at their respective proximal and distal ends, and since the branches 95 are self-biased to be space apart from each other in their respective semi-circular shapes depicted in FIG. 2, the branches 95 when joined together at their distal ends form an electrode loop 45, as discussed above with respect to FIG. 1. The electrode loop 45 may assume a generally oval shape when it is in its relaxed, biased shape depicted in FIG. 2.

As illustrated in FIG. 2, each branch 95 may be a mirror image of the other branch. Each branch 95 may include one or more electrodes 110 that act as pacing and/or sensing electrodes and are in electrical communication with respective electrical contacts 75, 80 of the lead connector end 70 via the electrical conductors that extend through the lead body 65. The sensing/pacing electrodes 110 may be formed of platinum, platinum-iridium alloy, MP35N, stainless steel, or other biocompatible electrically conductive metals. The electrodes 110 may be employed for cardiac resynchronization therapy on the LV as well as ATP, post shock passing, and anti-bradycardia pacing.

As shown in FIG. 2, each branch 95 may also include a shock electrode 115 that extends the length of, or a substantial portion of the length of, the branch 95. Each shock electrode 115 may be in the form of a smooth shock coil with a surface that provides little, if any, opening for tissue ingrowth. The shock electrode 115 may be formed of platinum, platinum-iridium alloy, MP35N, stainless steel, or other biocompatible electrically conductive metals. The shock electrode 115 may be a coiled conductor that is backfilled to prevent tissue ingrowth, or the shock electrode may be a metal electrode with a continuous, unbroken surface to prevent tissue ingrowth. The shock electrode 115 may be employed for defibrillation purposes.

Figure 3:
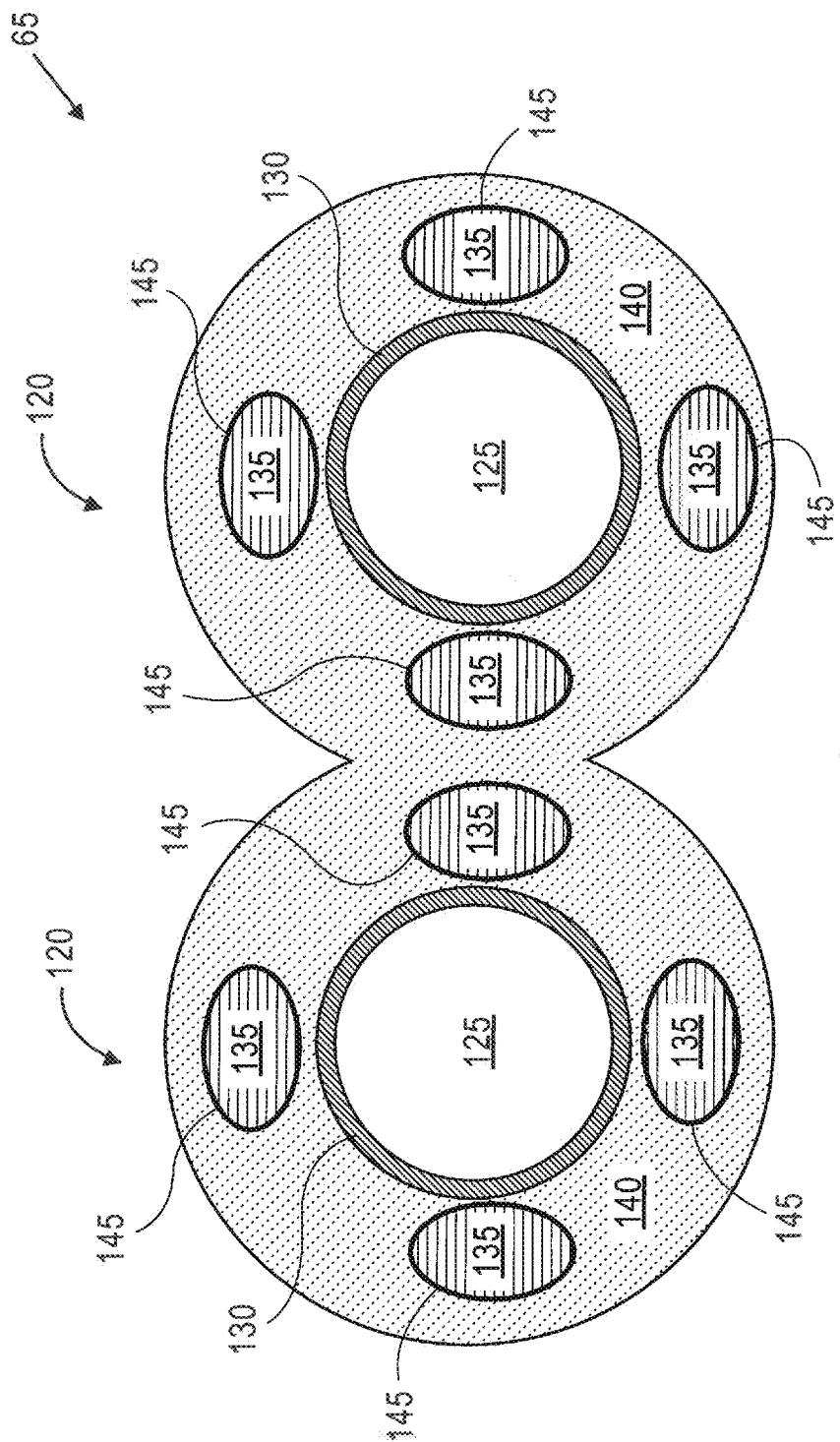
FIG. 3 is a transverse cross section of the lead body 65 as taken along section line 3-3 in FIG. 2.

As can be understood from FIG. 3, which is a transverse cross section of the lead body 65 as taken along section line 3-3 in FIG. 2, the lead body 65 includes a pair of sub-bodies 120 fused or otherwise joined together between the distal end of the lead connector end 70 and the proximal intersection of the branches 95. Each sub-body 120 includes a central stylet lumen 125, which may be in the form of a Polytetrafluoroethylene ("PTFE") tube 130. Radially outward of the central stylet lumen 125, each sub-body 120 also includes one to four or more electrical conductors 135 evenly distributed about the circumference of the central stylet lumen 125 and imbedded in a wall 140 formed of Optim™ insulation reflowed about the central stylet lumen 125 and the electrical conductors 135. The wall 140 of each sub-body 120 is fused or otherwise adhered or joined with the wall 140 of the other sub-body 120 such that the body 65 of the lead 50 is a single piece construction between the distal end of the lead connector end and the proximal intersection of the two branches.

Each electrical conductor 135 may be in the form of a Riata™ cable coiled as a quadrafiler and held together with a braid 145 made of Polyethylene Terephtyalate ("PET"). In one embodiment, filers of one or more of the electrical conductors 135 can be used in parallel to service the shock electrode 115 on the branch 95. Sensing/pacing electrodes 110 can also be serviced by the electrical conductors 135. In one embodiment, each branch 95 may support one, two, three, four or more sensing/pacing electrodes 110, and the number and configuration of the electrical conductors 135 will be configured accordingly.

While the embodiment depicted in FIG. 3 employs parallel stylet lumens 125 for the lead body 65, in other embodiments, the lead body 65 may have a single stylet lumen 125 that bifurcates into the branch stylet lumens of the lead body branches 95 or simply extends along a single branch 95, the other branch 95 not having a stylet lumen. In such embodiments, a single stiffer stylet could be used to deflect the electrode loop 45 as discussed below with respect to FIG. 5.

Figure 4:
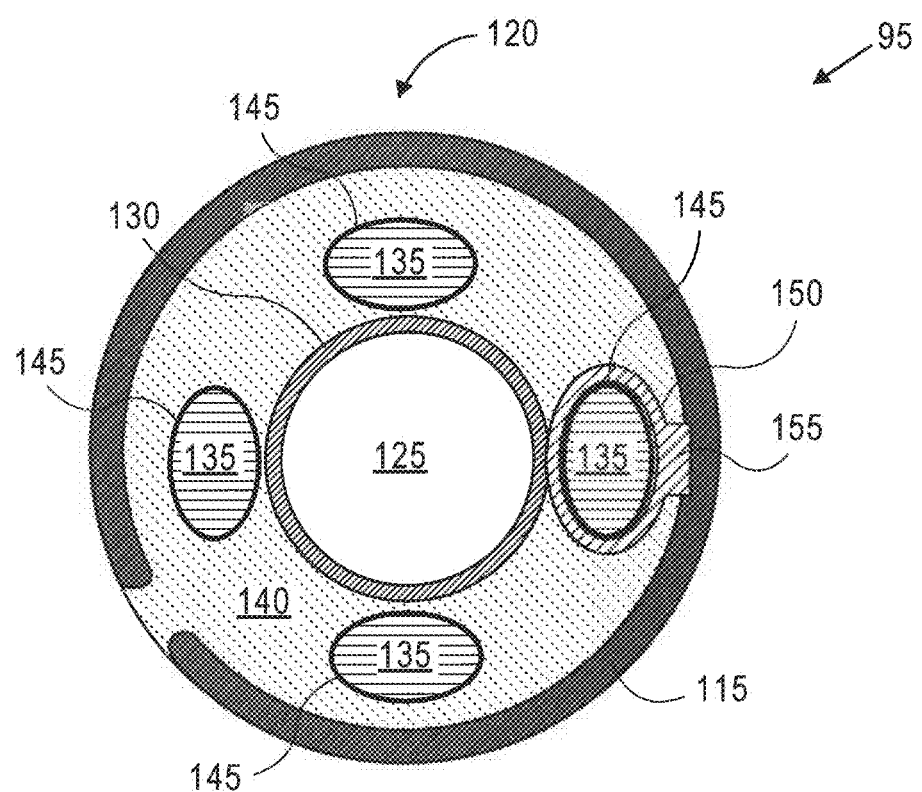
FIG. 4 is a transverse cross section of a representative branch of the lead body as taken along section lines 4-4 in FIG. 2.

As indicated in FIG. 4, which is a transverse cross section of a representative branch 95 of the lead body 65 as taken along section lines 4-4 in FIG. 2, each branch 95 includes only one of the pair of sub-bodies 120 since the pair of sub-bodies 120 are spaced apart in the region of the electrode loop 45. As is the case with each sub-body 120 where the sub-bodies are fused together as discussed with respect to FIG. 3, when each sub-body 120 is spaced apart from each other in the loop region 45, each sub-body includes a central stylet lumen 125, which may be in the form of a Polytetrafluoroethylene ("PTFE") tube 130. Radially outward of the central stylet lumen 125, each sub-body 120 also includes one to four or more electrical conductors 135 evenly distributed about the circumference of the central stylet lumen 125 and imbedded in a wall 140 formed of Optim™ insulation reflowed about the central stylet lumen 125 and the electrical conductors 135.

Again, each electrical conductor 135 may be in the form of a Riata™ cable coiled as a quadrafiler and held together with a braid 145 made of Polyethylene Terephtyalate ("PET"). In one embodiment, filers of one or more of the electrical conductors 135 can be used in parallel to service the shock electrode 115 on the branch 95. Sensing/pacing electrodes 110 can also be serviced by the electrical conductors 135.

As can be understood from FIG. 4, the shock electrode 115 may be in the form of a flat metal ribbon wrapped around the body of the branch 95 such that tissue ingrowth has little to no space to adhere to the shock electrode. Alternatively, the shock electrode 115 may formed via centerless grinding to result in a shock electrode with a smooth, semi-circular cross section.

As indicated in FIG. 4, a crimp sleeve 150 is crimped onto the adjacent electrical conductor 135 and laser welded to the underside of the shock electrode 115 or, alternatively, to a ring 150 that is laser welded to the underside of the shock electrode 115. The crimp sleeve 150 may include the ring 155, and the ring may provide a termination point for the shock electrode 115. If the ring 155 is in the middle of the shock electrode, the lead may have a reduced tendency to heat under MRI. Depending on the embodiment, the crimp sleeve and ring may be formed of platinum or any of the aforementioned biocompatible, electrically conductive metals.

As already mentioned above with respect to FIG. 2, the branches 95 of the electrode loop 45 are biased to be spaced apart from each other, each branch 95 assuming an arcuate or semi-circular configuration in its relaxed, non-deflected state when not acted upon by an outside force. It is this relaxed, looped configuration of the electrode loop 45 that is the configuration of the loop 45 when it is implanted on the epicardial surface of the patient heart, as can be understood from FIG. 1.

Figure 5:
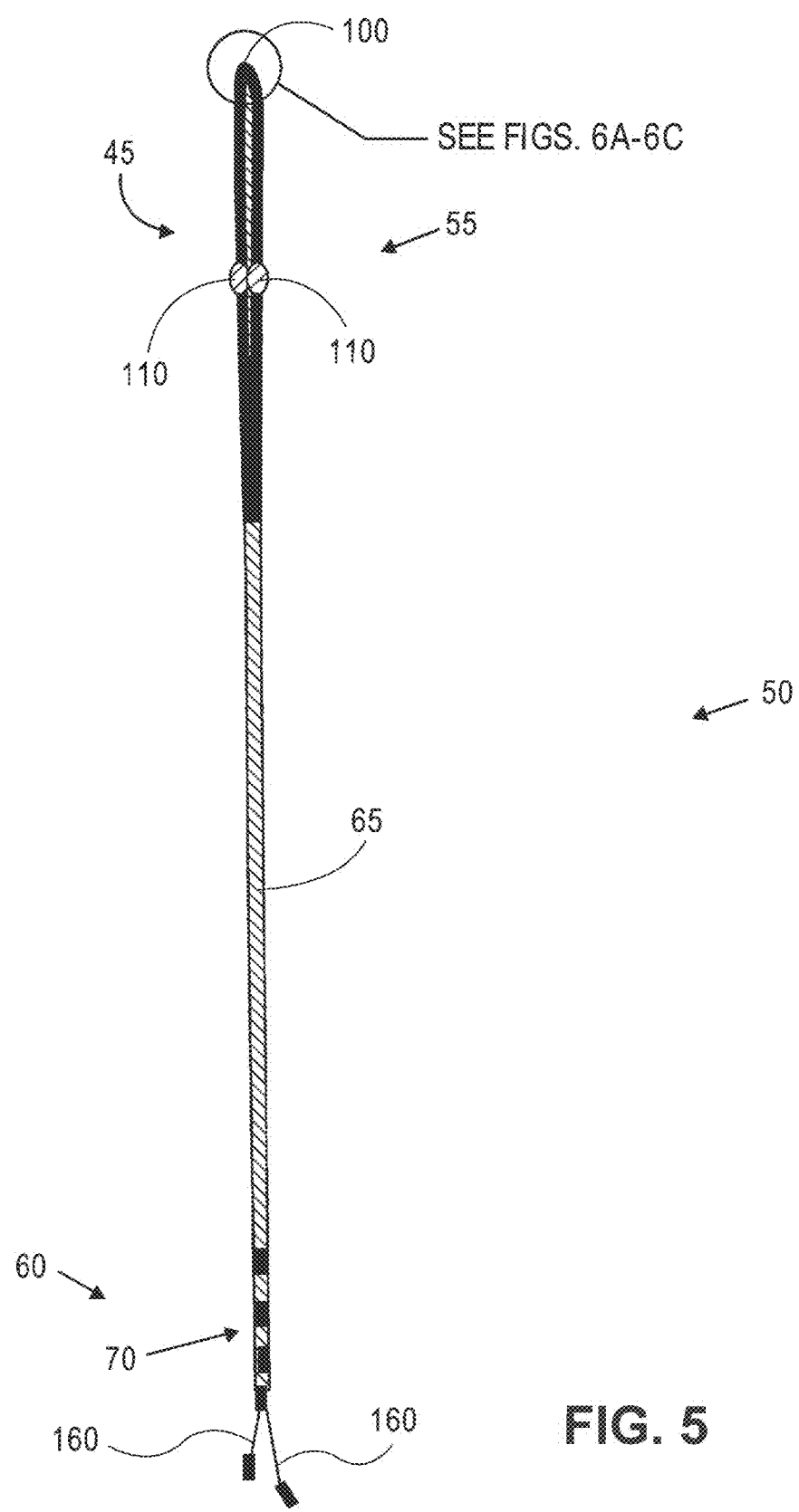
FIG. 5 is the same view of the lead depicted in FIG. 2, except showing the branches of the electrode loop being acted upon by a pair of stylets.

FIG. 5 is the same view of the lead 50 as depicted in FIG. 2, except showing the branches 95 of the electrode loop 45 being acted upon by a pair of stylets 160. As can be understood from FIGS. 3-5, the parallel stylet lumens 125 extend the length of the lead body 65 and through respective branches 95 forming the electrode loop 45 and allow for the receipt of respective stylets 160 that can be used to deflect the loop 45 from its relaxed, biased looped configuration of FIG. 2 to the linear configuration illustrated in FIG. 5. Specifically, the stylets 160 can be used to deflect the branches 95 such that they are not arcuate or semi-circular and are not spaced apart from each other. Instead, deflection via the stylets 160 causes the branches 95 to be generally linearly straight, as illustrated in FIG. 5. Such deflection of the loop 45 via application of a stylet 160 in each of the stylet lumens 125 can be used during the implantation of the lead 50 when the lead is passed through a lumen of a catheter/sheath/introducer or an access hole in the patient anatomy.

In other words, by pushing the stylets into the stylet lumens, the electrode loop closes as shown in FIG. 5 and the lead slides easily through a tubular body delivery device, such as, for example, a sheath, catheter or introducer for delivery to the implant site. Once the lead is in the pericardial space and located at the implant site, removing the stylets will allow the electrode loop to self-bias to its open configuration as depicted in FIGS. 1 and 2. The stylets can be steerable in order to position the tip of the electrode loop in the desired position before pulling the stylet to allow the electrode loop to self-expand.

Figure 6A:
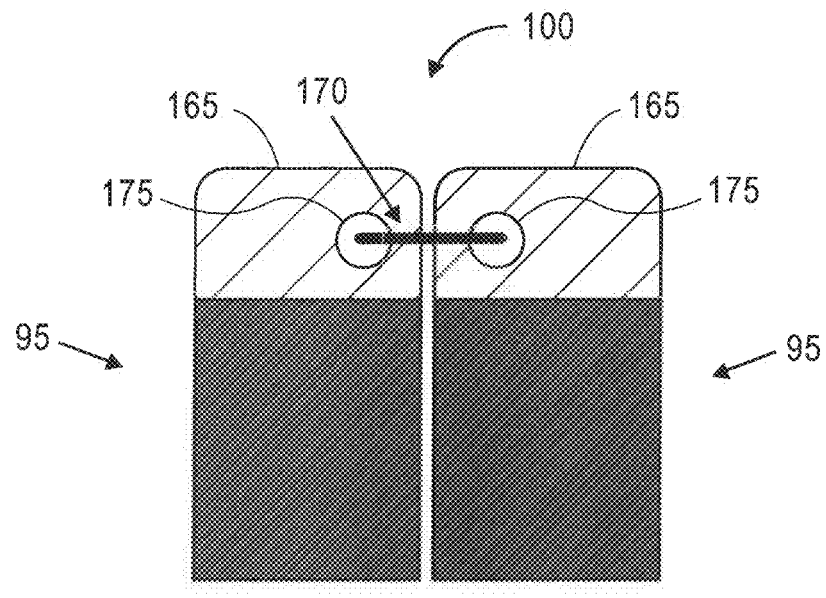
FIGS. 6A and 6B are enlarged views of the distal tips of the lead of FIG. 5, wherein a tip coupling arrangement employs one or more filaments.

FIG. 6A is an enlarged view of the distal tip 100 of the lead 50 of FIG. 5, wherein a first type of tip coupling arrangement is employed. As indicated in FIG. 6A, the distal end 165 of each electrode loop branch 95 is joined to the distal end 165 of the other electrode loop branch 95 by a filament 170 extending between respective anchoring locations (e.g., holes) 175. Thus, the filament 170 couples the branch distal ends 165 together and maintains the branches 95 in the looped configuration of the electrode loop 45 of the lead 50, as depicted in FIGS. 1 and 2.

Figure 7:
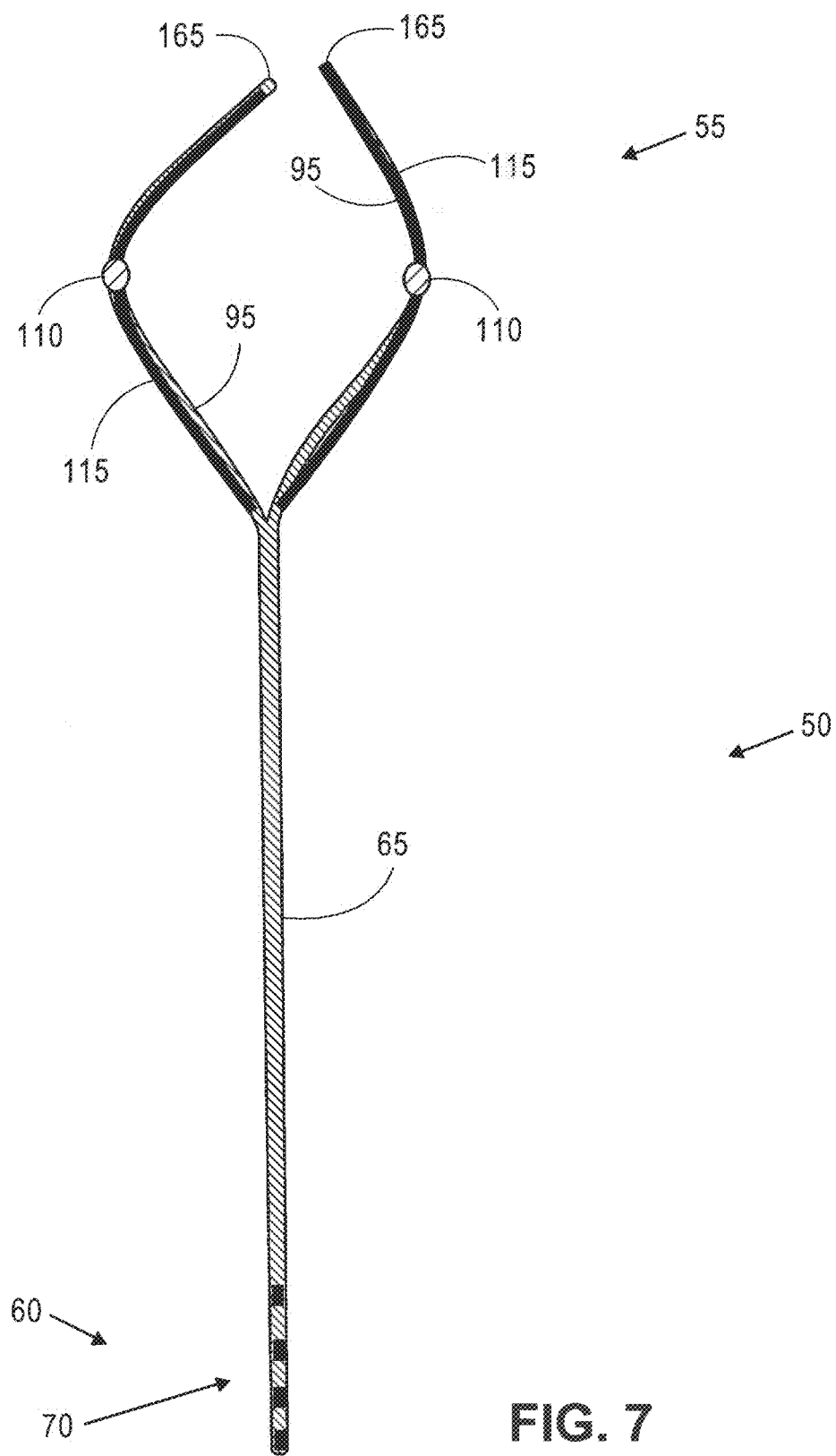
FIG. 7 is the same view of the lead depicted in FIGS. 2 and 5, except illustrating the branch distal ends being disconnected from each other.

In one embodiment, the filament will break under about 150 grams or 150,000 dynes of tension. This allows the branch distal ends 165 to decouple and the electrode loop 45 to open when the lead 50 is pulled upon by the explanter, as illustrated in FIG. 7, which is the same view of the lead 50 depicted in FIGS. 2 and 5, except illustrating the branch distal ends 165 being disconnected from each other. With the branches 95 decoupled at their respective distal ends 165 as indicated in FIG. 7, the branches 95 are able to slip out of the implant site upon explant of the lead 50.

Figure 6B:
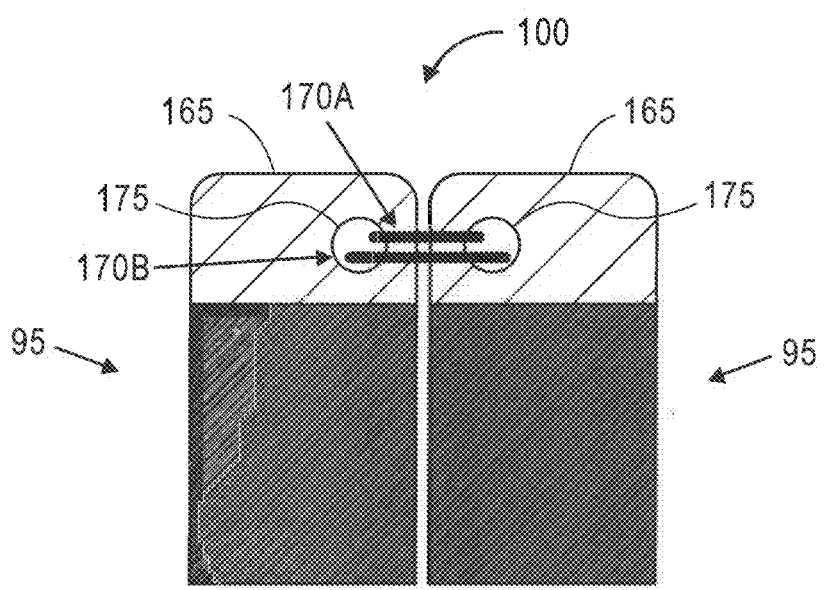

In one embodiment, as can be understood from FIG. 6B, which is the same view as FIG. 6A, the tip coupling arrangement may employ two filaments 170A, 170B looped through the holes 175, one tight or short loop 170A and one loose or long loop 170B. Such a dual loop arrangement provides some stepped coupling redundancy for the electrode loop 45. In other words, the dual loop arrangement of FIG. 6B provides a stepped backup mechanism for holding the electrode loop 45 of the lead 50 together during implantation. On account of the stepped loop arrangement employed in the lead distal end of FIG. 6B, if the implanter uses too much force and the tight loop 170A fails such that the electrode loop 45 opens up slightly, the electrode loop 45 still remains looped during implant on account of the loose loop 170B and the implanter is alerted to the fact that less force needs to be employed as the implantation continues.

Figure 6C:
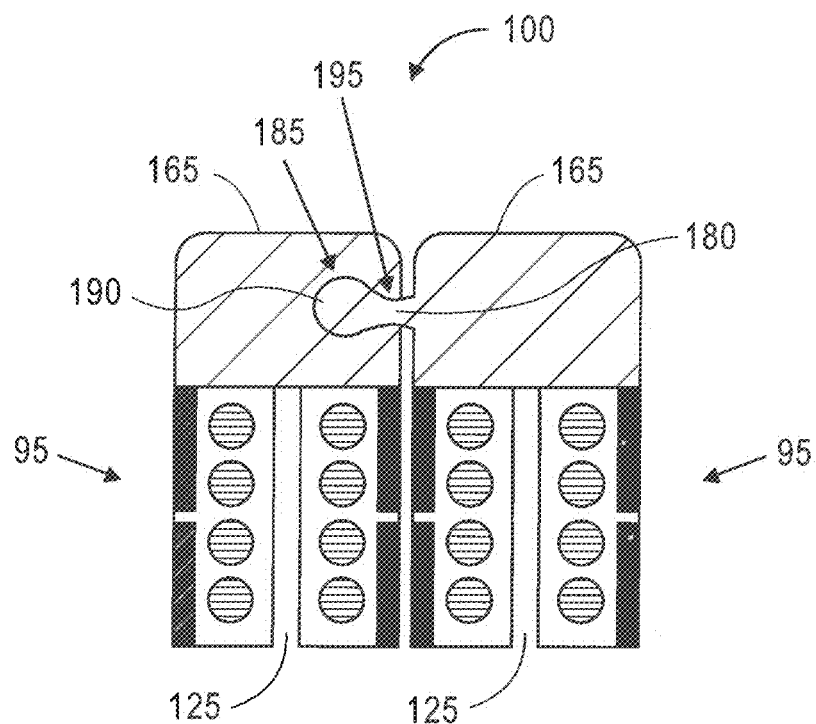
FIG. 6C is an enlarged view of the distal tip of the lead of FIG. 5, wherein a tip coupling arrangement employs an interference fit.

FIG. 6C is an enlarged longitudinal cross section of the distal tip 100 of the lead 50 of FIG. 5, wherein a tip coupling arrangement employs an interference fit. Specifically, in one embodiment, the interference fit arrangement may be in the form of a male member 180 received in a female opening 185. The male member 180 may have an enlarged free end 190 that snap-fits with a reduced diameter neck 195 of the female opening 185. The two branches distal ends 165 snap apart when the lead 50 is tugged on by the physician during explantation. The interference fit may decouple under about 150 grams or 150,000 dynes of tension.

Figure 6D:
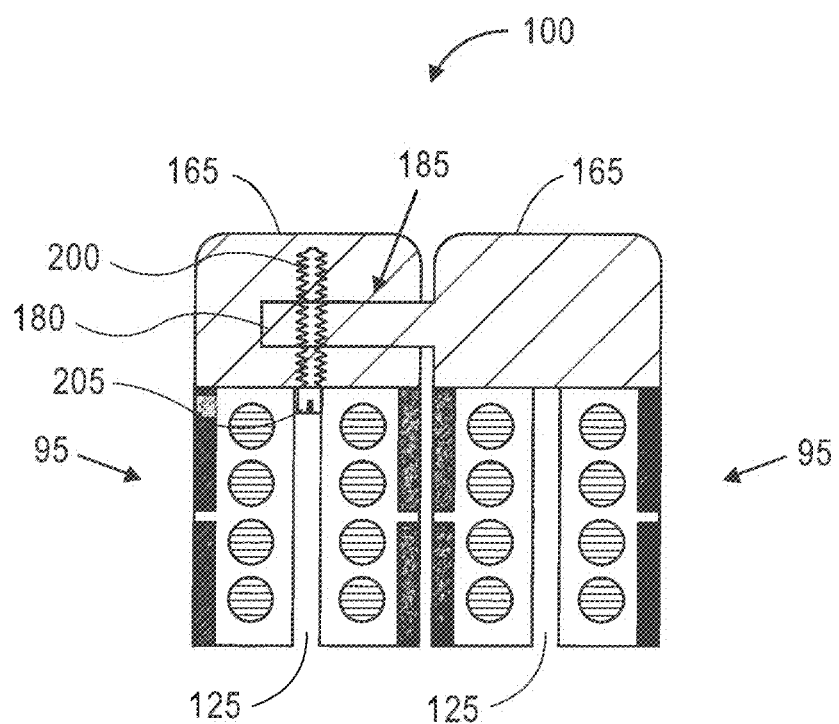
FIG. 6D is an enlarged view of the distal tip of the lead of FIG. 5, wherein a tip coupling arrangement employs a set screw.

FIG. 6D is an enlarged longitudinal cross section of the distal tip 100 of the lead 50 of FIG. 5, wherein a tip coupling arrangement employs a setscrew 200. In one embodiment, the setscrew arrangement may be in the form of a male member 180 received in a female opening 185 and the setscrew 200 extends from an extreme distal end of a stylet lumen 125 through the male member 180 when the male member 180 extends fully into the female opening 185. A head 205 of the setscrew 200 can be interfaced with by a screwdriver tip of a stylet, and the stylet can be used to remove the setscrew 200 from the male member 180, thereby allowing the male member to be withdrawn from the female opening and the branch distal ends 165 to separate as shown in FIG. 7 for explant of the lead 50 from the patient.

Figure 6E:
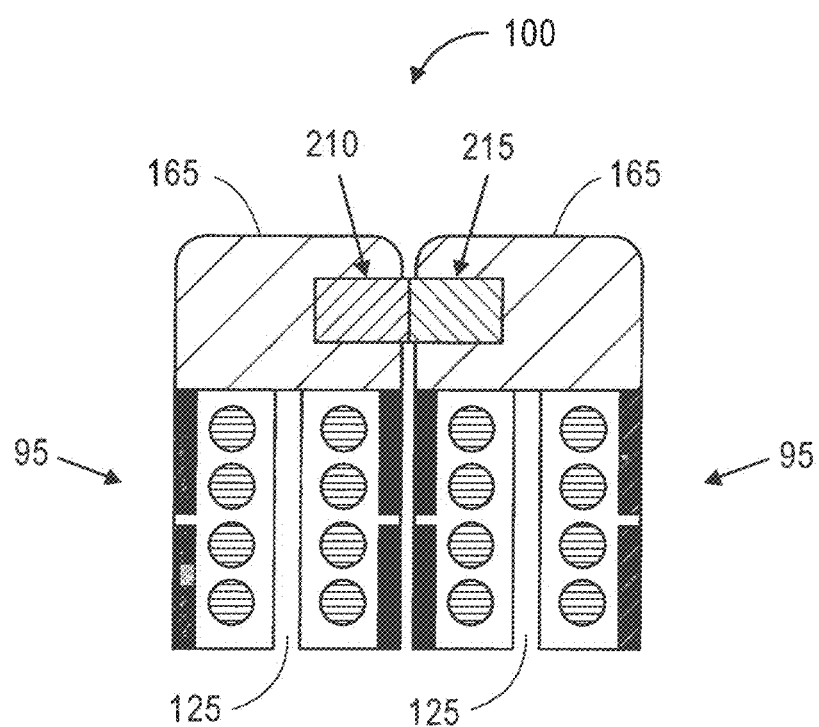
FIG. 6E is an enlarged view of the distal tip of the lead of FIG. 5, wherein a tip coupling arrangement employs magnetic coupling.

FIG. 6E is an enlarged view of the distal tip 50 of the lead of FIG. 5, wherein a tip coupling arrangement employs magnetic coupling. For example, in one embodiment, the magnetic coupling may include a first magnetic portion 210 located on one of the branches 95 and a second magnetic portion 215 located on the other of the branches 95. The magnetic portions 210, 215 are arranged such that they may magnetically couple with each other when the branch distal ends are coupled together as indicated in FIG. 6E. In one embodiment, both magnetic portions 210, 215 are magnets while in other embodiments one of the magnetic portions 210, 215 is a magnet while the other of the magnetic portions 210, 215 is a metal that is capable of being attracted via the magnetism of the magnet. In one embodiment, the magnet(s) of the magnetic portions 210, 215 includes Neodymium, which may be coated with a biocompatible material, or have a shell made of, PTFE, Titanium, stainless steel, or etc. The magnetic portions 210, 215 of the two branches distal ends 165 decouple when the lead 50 is tugged on by the physician during explantation. The magnetic portions 210, 215 may decouple under about 150 grams or 150,000 dynes of tension.

While the embodiment depicted in FIGS. 2, 5 and 7 illustrates an electrode loop 45 wherein the branches 95 are substantially, if not completely, equal in length, in other embodiments, the branches 95 may be unequal with respect to length. For example, as indicated in FIG. 8A, which is the same view as depicted in FIG. 7, except of another electrode loop embodiment and more schematic in nature such that the electrodes 110, 115 and lead connector end 70 are not illustrated, one branch 95 may be substantially longer than the other branch 95 such that, for example, one branch forms three quarters of the electrode loop and the other branch 95 forms one quarter of the electrode loop.

Figure 8A:
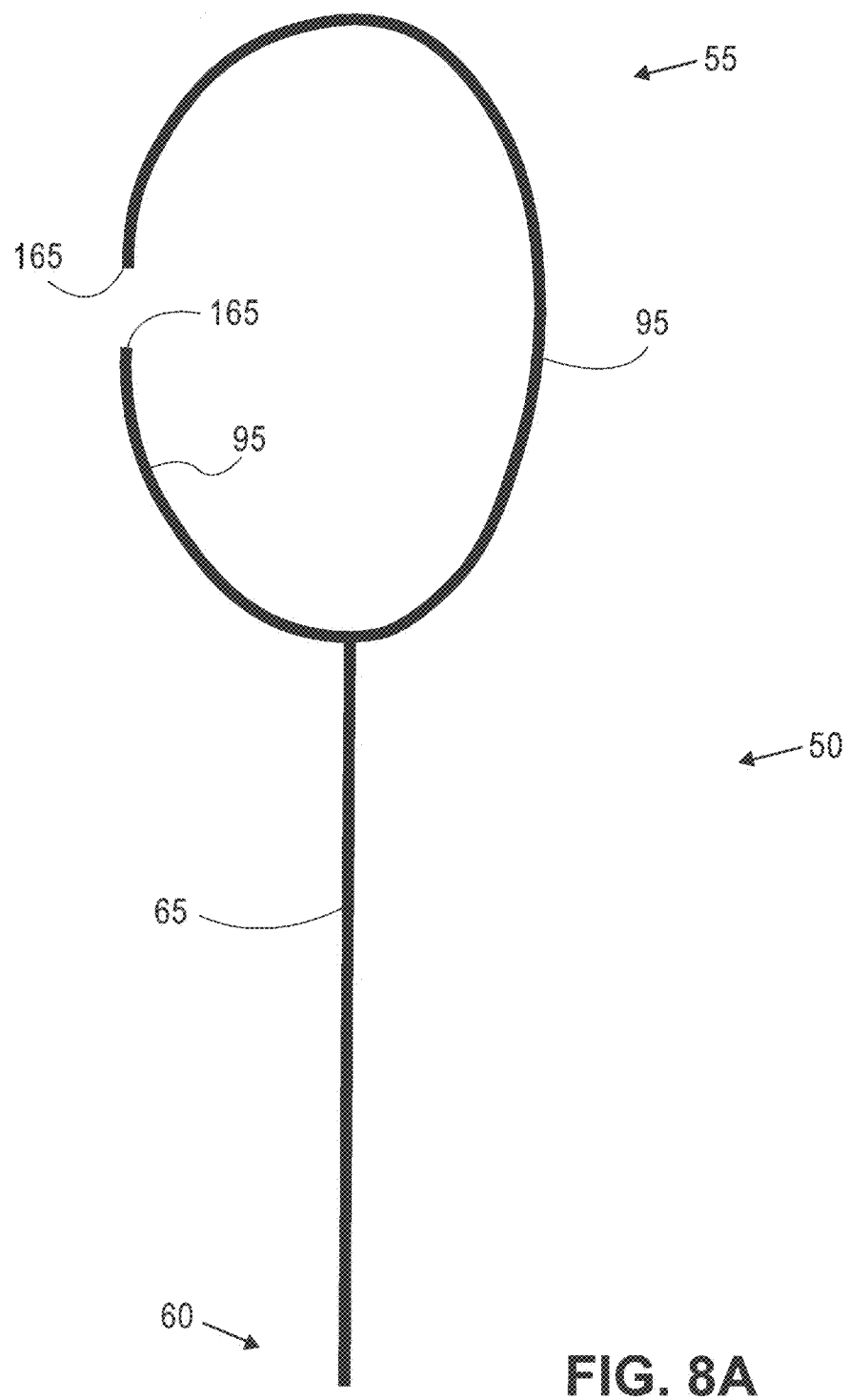
FIGS. 8A and 8B are the same view as depicted in FIG. 7, except of other electrode loop embodiments and more schematic in nature such that the electrodes and lead connector ends are not illustrated.
Figure 8B:
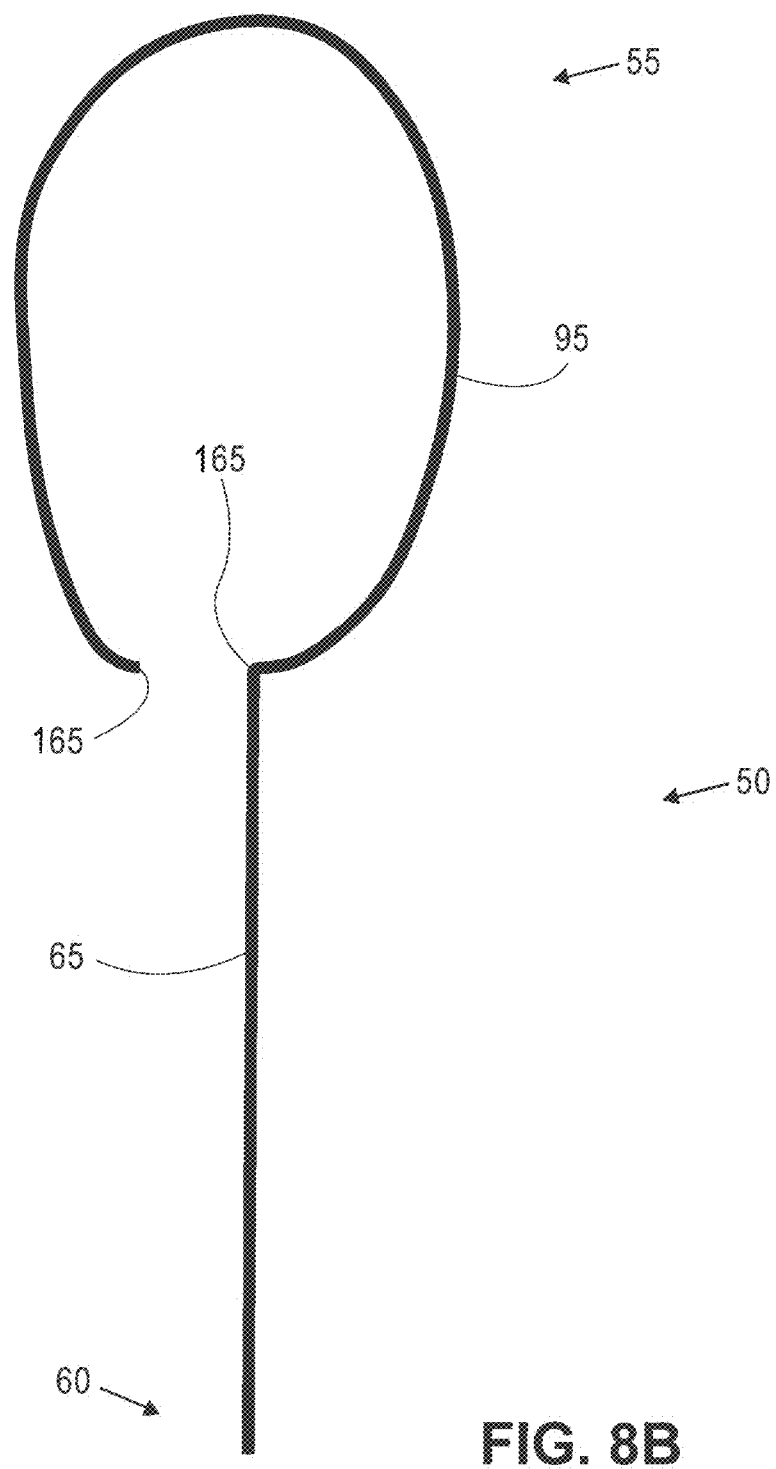

As illustrated in FIG. 8B, which is the same type of view as FIG. 8A, except of another embodiment, one branch 95 may form essentially the entirety of the electrode loop while the other branch 95 is essentially nonexistent or a numb that is only present and sufficient in size to allow for the components of any one or more of the above-described coupling arrangements to be supported between the distal ends 165 of the branches 95 for coupling the distal ends 165 together to form an electrode loop 45 from the branches 95 similar to shown with respect to FIG. 2.

While FIGS. 8A and 8B do not illustrate the presence of electrodes 110, 115 or a lead connector end 70 like shown in FIGS. 2, 5 and 7, of course such elements and their locations are readily understandable by someone of skill in the art with respect to the embodiments depicted in FIGS. 8A and 8B.

Various other modifications and additions can be made to the exemplary implementations discussed without departing from the spirit and scope of the presently disclosed technology. For example, while the embodiments described above refer to particular features, the scope of this disclosure also includes implementations having different combinations of features and implementations that do not include all of the described features. Accordingly, the scope of the presently disclosed technology is intended to embrace all such alternatives, modifications, and variations together with all equivalents thereof.

What is claimed is:

1. An implantable lead configured to administer electrotherapy to a patient heart from an implantable pulse generator, the lead comprising:
   a lead body including a bifurcated distal region including first and second lead body branches each terminating in a distal end, each of the first and second body branches being biased to each assume an arcuate shape, at least one of the first lead body branch or second lead body branch including an electrode;
   the lead body further including first and second stylet lumens running parallel to each other, the first stylet lumen extending along the first lead body branch and the second stylet lumen extending along the second lead body branch; and
   an attachment structure coupling together the distal ends of the first and second lead body branches, the attachment structure being configured to release such that the distal ends of the first and second lead body branches can decouple from each other.

2. The lead of claim 1, wherein the first and second lead body branches are biased to be spaced apart from each other when the distal ends are coupled together via the attachment structure.

3. The lead of claim 1, wherein the first and second lead body branches are biased to form a generally oval loop when the distal ends are coupled together via the attachment structure.

4. The lead of claim 1, wherein the lead body includes a single stylet lumen that bifurcates into first and second branch stylet lumens, the first stylet branch lumen extending along the first lead body branch and the second stylet branch lumen extending along the second lead body branch.

5. The lead of claim 1, wherein the attachment structure includes a first filament coupling together the first and second lead body branches near the distal ends of the first and second lead body branches.

6. The lead of claim 5, wherein the attachment structure further includes a second filament coupling together the first and second lead body branches near the distal ends of the first and second lead body branches, the second filament having a length that is longer than the first filament.

7. The lead of claim 1, wherein the attachment structure includes an interference fit coupling structure.

8. The lead of claim 7, wherein the interference fit coupling structure includes a male member that snap-fits into a female opening, the male member being part of the first lead body branch near the distal end thereof, and the female opening being part of the second lead body branch near the distal end thereof.

9. The lead of claim 1, wherein the attachment structure includes a setscrew coupling structure, the setscrew coupling structure includes a setscrew and a male member that is received in a female opening, the setscrew preventing the male member from withdrawing from the female opening unless the setscrew is unscrewed to release the male member.

10. The lead of claim 9, wherein a head of the setscrew is accessible via a stylet lumen extending through one of the first or second lead body branches.

11. The lead of claim 1, wherein the attachment structure includes a magnetic coupling structure.

12. The lead of claim 1, further comprising a lead connector end extending proximally from a proximal end of the lead body, the lead connector end configured to couple to the implantable pulse generator.

13. A method of explanting an implantable electrotherapy lead from an implantation site, the method comprising:
   decoupling from each other first and second branch distal ends of a bifurcated distal region of a lead body, the decoupling further including breaking a filament that extends between the first and second branch distal ends, the decoupling causing a snap-fit arrangement between a male member of the first branch distal end and a female opening of the second branch distal end to disengage by the male member leaving the female opening; and
   withdrawing the lead from the implantation site.

14. The method of claim 13, wherein the decoupling includes causing a setscrew to release from a male member of the first branch distal end such that the male member can be removed from a female opening of the second branch distal end, and further wherein the decoupling further includes extending a stylet down a stylet lumen of the lead to cause the setscrew to release the male member.

15. The method of claim 13, wherein the decoupling includes overcoming a magnetic bond between the first and second branch distal ends.

16. An implantable lead configured to administer electrotherapy to a patient heart from an implantable pulse generator, the lead comprising:

a lead body including a bifurcated distal region including first and second lead body branches each terminating in a distal end, at least one of the first lead body branch or second lead body branch including an electrode; and an attachment structure coupling together the distal ends of the first and second lead body branches, the attachment structure being configured to release such that the distal ends of the first and second lead body branches can decouple from each other;

the lead body including first and second stylet lumens running parallel to each other, the first stylet lumen extending along the first lead body branch and the second stylet lumen extending along the second lead body branch;

the attachment structure including an interference fit coupling structure, the interference fit coupling structure including a male member that snap-fits into a female opening, the male member being part of the first lead body branch near the distal end thereof, and the female opening being part of the second lead body branch near the distal end thereof.

* * * * *